(12) United States Patent
Kawata (10) Patent No.: US 6,542,627 B1
(45) Date of Patent: Apr. 1, 2003

(54) MEDICAL IMAGE OUTPUT SYSTEM

(75) Inventor: Masayuki Kawata, Kaisei-machi (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/655,406

(22) Filed: Sep. 5, 2000

Related U.S. Application Data (63) Continuation-in-part of application No. 09/560,882, filed on Apr. 28, 2000, now abandoned.

(30) Foreign Application Priority Data

Apr. 28, 1999 (JP) .......................................... 11-122375
Apr. 28, 2000 (JP) ...................................... 2000-129695

(51) Int. Cl.$^7$ .............................................. G06K 9/00
(52) U.S. Cl. ...................................... 382/128; 128/922
(58) Field of Search ............................... 382/128, 131, 382/130, 132, 129; 128/922; 600/300, 310, 407

(56) References Cited

U.S. PATENT DOCUMENTS

| | | | |
|---|---|---|---|
| 4,602,333 A | * 7/1986 | Komori | ...................... 382/131 |
| 5,086,392 A | * 2/1992 | Nakajima | ................... 382/128 |
| 5,647,018 A | * 7/1997 | Benjamin | ................... 382/128 |

* cited by examiner

Primary Examiner—Bhavesh Mehta
Assistant Examiner—Abolfazl Tabatabai
(74) Attorney, Agent, or Firm—Sughrue Mion, PLLC

(57) ABSTRACT

A medical image output system comprises a first storage device for storing medical image signals, each of which represents a medical image of a patient. A second storage device stores photographic image signals, each of which represents a photographic image of a somatic feature of a patient, and/or photographic image signals, each of which represents a photographic image of a person associated with a patient, such that it is clear which photographic image signal corresponds to which medical image signal stored in the first storage means. An output device operates such that, in cases where the output device outputs a medical image signal representing a medical image of a certain patient from the first storage device, the output device also outputs the photographic image signal, which corresponds to the outputted medical image signal, from the second storage device. With the medical image output system, it is easy to recognize whether the medical image is or is not the image of a patient to be subjected to a diagnosis.

8 Claims, 6 Drawing Sheets

MEDICAL IMAGE OUTPUT SYSTEM

This application is a continuation-in-part application of application Ser. No. 09/560,882 filed Apr. 28, 2000 now abandoned.

BACKGROUND OF THE INVENTION

1. Field of the Invention

This invention relates to a medical image output system for outputting a medical image signal representing a medical image of a patient.

2. Description of the Related Art

In conventional medical image output systems for outputting medical image signals of patients, medical images of patients are recorded, and medical image signals representing the medical images of the patients are stored in a data base. When necessary, a medical image signal is read from the data base and utilized for reproducing the medical image, which is represented by the medical image signal, as a visible image on a monitor or printing the medical image as a hard copy. The reproduced medical image is utilized in making a diagnosis of an illness. In such cases, signal retrieval is performed in accordance with information, such as the name of the patient or the identification (ID) number of the patient, and the medical image signal corresponding to the patient to be subjected to a diagnosis is thereby read from the data base and utilized for reproducing the medical image of the patient. In cases where image patterns representing the name of the patient or the ID number of the patient are reproduced together with the medical image of the patient, it can be confirmed whether the reproduced medical image is or is not the image of the patient to be subjected to a diagnosis.

However, when a medical image signal corresponding to the patient to be subjected to a diagnosis is to be read from the data base, it often occurs that an incorrect name of patient or an incorrect ID number of patient is inputted by mistake. Also, it often occurs that medical image signals corresponding to different patients of the same name are stored in the data base. Therefore, there is the risk that the reproduced medical image will not be the image of the patient to be subjected to a diagnosis. In such cases, if the image patterns representing the name of the patient or the ID number of the patient, which are reproduced together with the medical image of the patient, are confirmed strictly, it can be recognized that the reproduced medical image is not the image of the patient to be subjected to a diagnosis. However, with the name of the patient or the ID number of the patient, it is not easy to discriminate at a glance whether the name of the patient or the ID number of the patient is or is not that of the patient to be subjected to a diagnosis. Therefore, there is the risk that a diagnosis or a surgical operation will be performed on a patient in accordance with a medical image of a different patient, and a serious medical trouble will occur.

SUMMARY OF THE INVENTION

The primary object of the present invention is to provide a medical image output system, wherein a medical image represented by a medical image signal is capable of being reproduced such that it is easy to recognize whether the medical image is or is not the image of a patient to be subjected to a diagnosis.

The present invention provides a medical image output system, comprising:

i) first storage means for storing medical image signals, each of which represents a medical image of a patient, ii) second storage means for storing photographic image signals, each of which represents a photographic image of a somatic feature of a patient, and/or photographic image signals, each of which represents a photographic image of a person associated with a patient, such that it is clear which photographic image signal corresponds to which medical image signal stored in the first storage means, and iii) output means for operating such that, in cases where the output means outputs a medical image signal representing a medical image of a certain patient from the first storage means, the output means also outputs the photographic image signal, which corresponds to the outputted medical image signal, from the second storage means.

In the medical image output system in accordance with the present invention, single storage means may act as both the first storage means and the second storage means. Alternatively, two independent storage means may be provided as the first storage means and the second storage means.

The term "photographic image of a somatic feature of a patient" as used herein means the image of the feature of the patient, such as the image of the face of the patient or the image of the fingerprint of the patient, which image has one to one correspondence to the patient. The term "photographic image of a person associated with a patient" as used herein means the image of the face of a member of the patient's family attending on the patient, the image of the face of the nurse in charge, the image of the face of the medical doctor in charge, or the like, which image has one to one correspondence to the patient. In cases where there are a plurality of persons associated with the patient, the photographic image signal may be stored for each of the persons associated with the patient.

The medical image output system in accordance with the present invention should preferably be modified such that, in cases where both the photographic image signals, each of which represents a photographic image of a somatic feature of a patient, and the photographic image signals, each of which represents a photographic image of a person associated with a patient, are stored in the second storage means, the output means operates such that, when the output means outputs the medical image signal representing the medical image of the certain patient from the first storage means, the output means also outputs both the photographic image signal, which represents the photographic image of the somatic feature of the certain patient, and the photographic image signal, which represents the photographic image of the person associated with the certain patient, from the second storage means.

In such cases, the photographic image signals, each of which represents a photographic image of a somatic feature of a patient, and the photographic image signals, each of which represents a photographic image of a person associated with a patient, are stored in the second storage means, such that it is clear which photographic image signal representing a photographic image of a somatic feature of a patient corresponds to which photographic image signal representing a photographic image of a person associated with a patient.

Also, in such cases, the second storage means may comprise means for storing the photographic image signals, each of which represents a photographic image of a somatic feature of a patient, and means for storing the photographic image signals, each of which represents a photographic image of a person associated with a patient.

Further, the medical image output system in accordance with the present invention should preferably further comprise reproduction means for receiving the medical image signal and the corresponding photographic image signal from the output means, reproducing the medical image as a visible image from the received medical image signal, and reproducing the photographic image as a visible image from the corresponding photographic image signal.

In cases where the medical image and the photographic image are reproduced respectively from the medical image signal and the corresponding photographic image signal, the medical image and the photographic image may be reproduced on a single output medium. Alternatively, the medical image and the photographic image may be reproduced on two independent output media. For example, in cases where the output medium is a photosensitive material, the medical image and the photographic image may be printed on a single sheet of the photosensitive material. Alternatively, the medical image and the photographic image may be printed on two independent sheets of the photosensitive material. In cases where the medical image and the photographic image are printed on two independent sheets of the photosensitive material, the printed photographic image should preferably be attached to the printed medical image or a bag, or the like, which accommodates the printed medical image.

In cases where both the photographic image signal, which represents the photographic image of the somatic feature of a certain patient, and the photographic image signal, which represents the photographic image of the person associated with the certain patient, are received from the output means, the reproduction means reproduces both the photographic image of the somatic feature of the certain patient and the photographic image of the person associated with the certain patient as visible images from the received photographic image signals. In cases where there are a plurality of photographic image signals, which represent photographic images of persons associated with the certain patient, all of the photographic images of the persons associated with the certain patient may be reproduced as the visible images from the photographic image signals. Alternatively, only a representative photographic image (e.g., a photographic image of a member of the patient's family attending on the patient) among the photographic images of the persons associated with the certain patient may be reproduced as a visible image.

Furthermore, the medical image output system in accordance with the present invention should preferably further comprise request means for operating such that, in cases where a certain photographic image signal has not been updated for a predetermined period after the certain photographic image signal was stored in the second storage means, the request means makes a request for storing a new photographic image signal in the second storage means.

In order for the request to be made by the request means, for example, an instruction for requesting the storing of the new photographic image signal may be displayed on the reproduction means or may be given with a voice.

With the medical image output system in accordance with the present invention, the photographic image signal, which represents the photographic image of the somatic feature of the patient, or the photographic image signal, which represents the photographic image of the person associated with the patient, is outputted together with the corresponding medical image signal. Therefore, when reference is made to the outputted photographic image signal, it can be confirmed immediately whether the outputted medical image signal is or is not the one representing the medical image of the patient to be subjected to a diagnosis. Accordingly, the problems can be prevented from occurring in that a diagnosis or a surgical operation is performed on a patient in accordance with a medical image of a different patient and a serious medical trouble occurs.

With the medical image output system in accordance with the present invention, wherein the medical image is reproduced as a visible image from the medical image signal and the photographic image is reproduced as a visible image from the corresponding photographic image signal, when the reproduced photographic image is seen, it can be confirmed at a glance whether the medical image is or is not the image of the patient to be subjected to a diagnosis.

Also, with the medical image output system in accordance with the present invention, in cases where both the photographic image signals, each of which represents a photographic image of a somatic feature of a patient, and the photographic image signals, each of which represents a photographic image of a person associated with a patient, are stored in the second storage means, both the photographic image signal, which represents the photographic image of the somatic feature of a certain patient, and the photographic image signal, which represents the photographic image of the person associated with the certain patient, may be outputted together with the corresponding medical image signal. In such cases, an increased number of pieces of information, with which the patient is capable of being confirmed, can be obtained. Therefore, the confirmation as to whether the outputted medical image signal is or is not the one corresponding to the patient to be subjected to a diagnosis can be made more accurately.

In cases where a comparatively long period has elapsed after a medical image signal corresponding to a certain patient was acquired, it may occur that the appearance of the patient changes, or the nurse in charge or the medical doctor in charge is altered. In such cases, if the medical image signal corresponding to the patient is outputted together with the photographic image signal, it will be difficult to make the confirmation as to whether the outputted medical image signal is or is not the one corresponding to the patient to be subjected to a diagnosis. In order for the aforesaid problems to be eliminated, with the medical image output system in accordance with the present invention, in cases where a certain photographic image signal has not been updated for a predetermined period after the certain photographic image signal was stored in the second storage means, a request for storing a new photographic image signal in the second storage means may be made by the request means. In this manner, the new photographic image signal can be stored in the second storage means. Therefore, even if the appearance of the patient changes, or the nurse in charge or the medical doctor in charge is altered, the confirmation can be made accurately as to whether the outputted medical image signal is or is not the one corresponding to the patient to be subjected to a diagnosis.

DESCRIPTION OF THE PREFERRED EMBODIMENTS

The present invention will hereinbelow be described in further detail with reference to the accompanying drawings.

Figure 1:
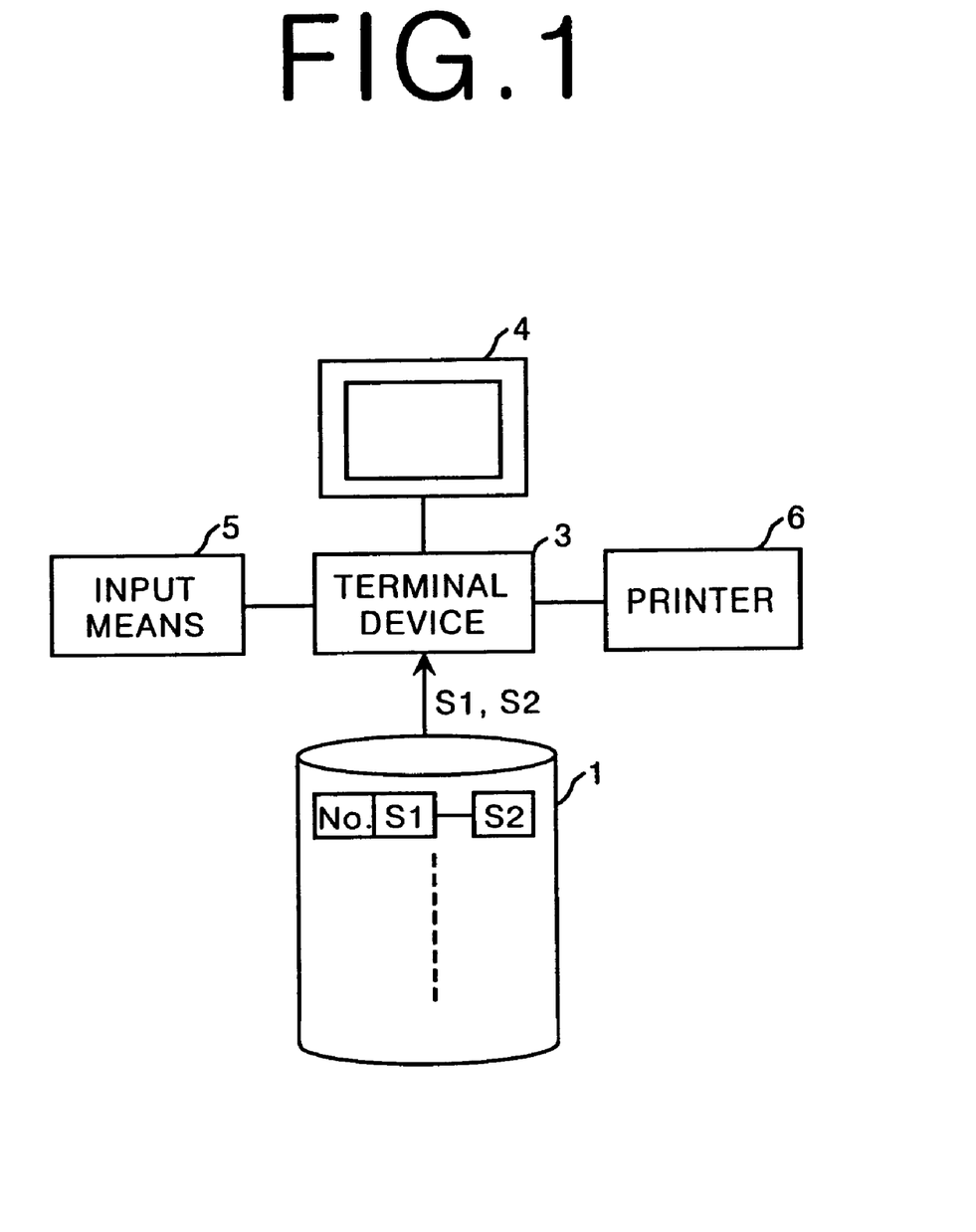
FIG. 1 is a schematic block diagram showing an embodiment of the medical image output system in accordance with the present invention.

FIG. 1 is a schematic block diagram showing an embodiment of the medical image output system in accordance with the present invention. As illustrated in FIG. 1, the medical image output system comprises a data base unit 1 and a terminal device 3. The data base unit 1 stores medical image signals S1, S1, . . . , each of which represents a medical image of a patient, and face image signals S2, S2, . . . , each of which represents a photographic face image of a patient, such that it is clear which face image signal S2 corresponds to which medical image signal S1. The terminal device 3 is utilized to read one of the medical image signals S1, S1, . . . and the corresponding face image signal S2 from the data base unit 1. The terminal device 3 is connected to a monitor 4 for reproducing the medical image and the face image respectively from the medical image signal S1 and the corresponding face image signal S2. The monitor 4 may be constituted of a cathode ray tube (CRT) display device, a liquid crystal panel, or the like. The terminal device 3 is also connected to input means 5, such as a keyboard and a mouse device, and a printer 6.

Figure 2:
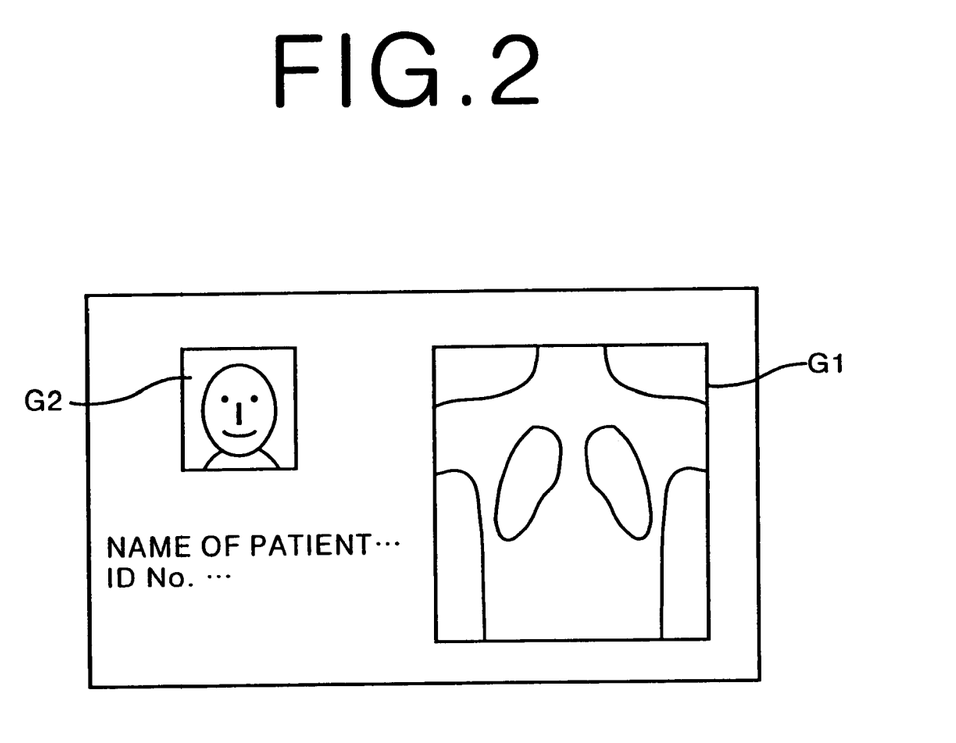
FIG. 2 is an explanatory view showing a medical image of a patient and a face image of the patient, which are reproduced on a monitor.

An ID number of a patient, the corresponding medical image signal S1, and the corresponding face image signal S2 are stored in the data base unit 1. The medical image signal S1 is obtained by, for example, recording a radiation image of the patient on a stimulable phosphor sheet and photoelectrically reading out the radiation image from the stimulable phosphor sheet. The face image signal S2 is obtained by, for example, taking a photograph of the face of the patient with a digital camera or photoelectrically reading out a photograph of the face of the patient with a scanner, or the like. When the ID number of the patient is inputted from the terminal device 3, the medical image signal S1, which corresponds to the ID number of the patient, and the face image signal S2, which corresponds to the medical image signal S1, are read from the data base unit 1 and fed into the terminal device 3. As illustrated in FIG. 2, on the monitor 4 connected to the terminal device 3, a medical image G1, which is represented by the medical image signal S1, and a face image G2, which is represented by the face image signal S2, are reproduced. The medical image G1 and the face image G2 are displayed together with the name of the patient and the ID number of the patient on the monitor 4.

Figure 3:
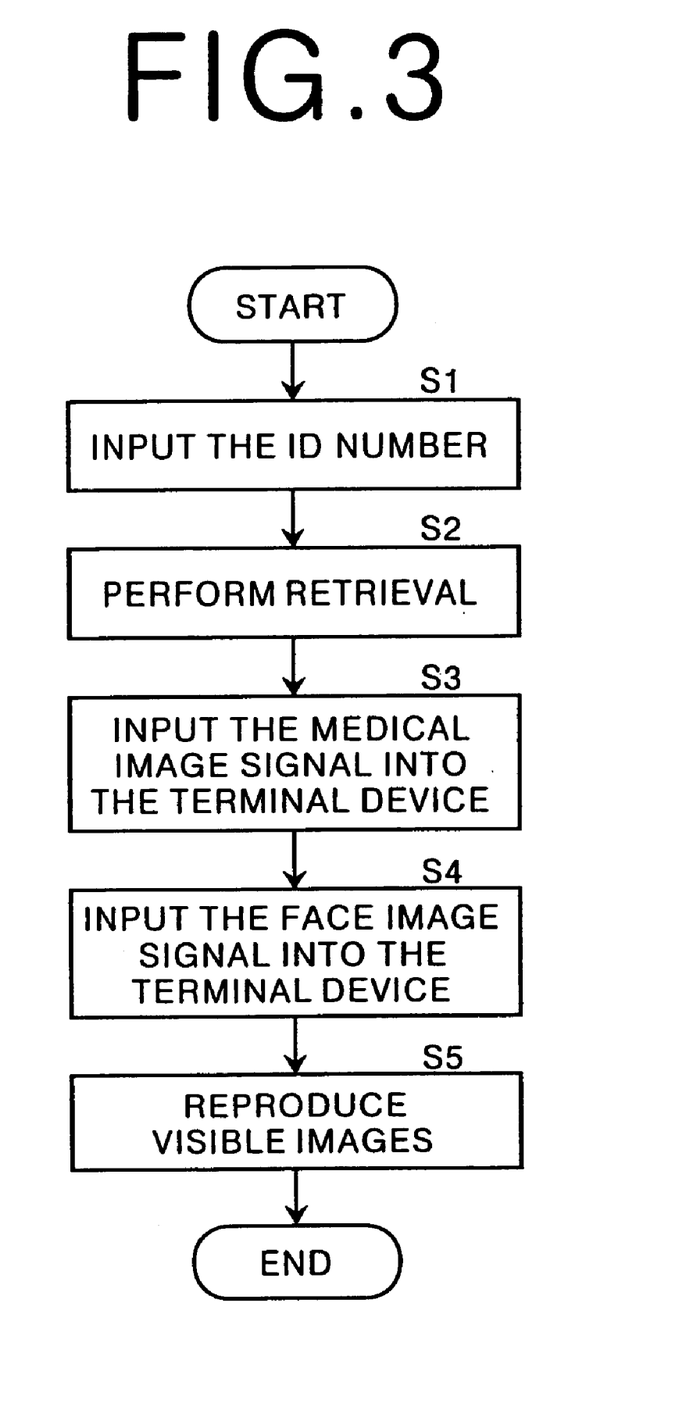
FIG. 3 is a flow chart showing how the embodiment of FIG. 1 operates.

How this embodiment operates will be described hereinbelow with reference to FIG. 3. FIG. 3 is a flow chart showing how the embodiment of FIG. 1 operates. Firstly, in a step S1, the ID number of the patient is inputted from the input means 5 connected to the terminal device 3, and the information representing the ID number of the patient is fed from the terminal device 3 into the data base unit 1. In a step S2, retrieval is performed in the data base unit 1 in accordance with the received information representing the ID number. In a step S3, the retrieved medical image signal S1 corresponding to the ID number is fed from the data base unit 1 into the terminal device 3. At this time, in a step S4, the face image signal S2 corresponding to the retrieved medical image signal S1 is also read from the data base unit 1 and fed into the terminal device 3. In a step S5, in the terminal device 3, the received medical image signal S1 and the received face image signal S2 are combined with each other, and the medical image G1 and the face image G2 are reproduced and displayed on the monitor 4 as illustrated in FIG. 2. The processing is finished with the step 5.

As described above, in this embodiment, when the medical image G1 is reproduced and displayed on the monitor 4, the face image G2 of the patient corresponding to the medical image G1 is also reproduced and displayed on the monitor 4. Therefore, it can be confirmed at a glance whether the reproduced medical image G1 is or is not the image of the patient to be subjected to a diagnosis. Accordingly, the problems can be prevented from occurring in that a serious medical trouble occurs due to a mix-up about who is to be subjected to a diagnosis.

In the embodiment described above, the medical image signals S1, S1, . . . and the face image signals S2, S2, . . . are stored in a single data base unit 1. Alternatively, the medical image signals S1, S1, . . . and the face image signals S2, S2, . . . may be stored in two independent data base units such that it is clear which face image signal S2 corresponds to which medical image signal S1.

Figure 4:
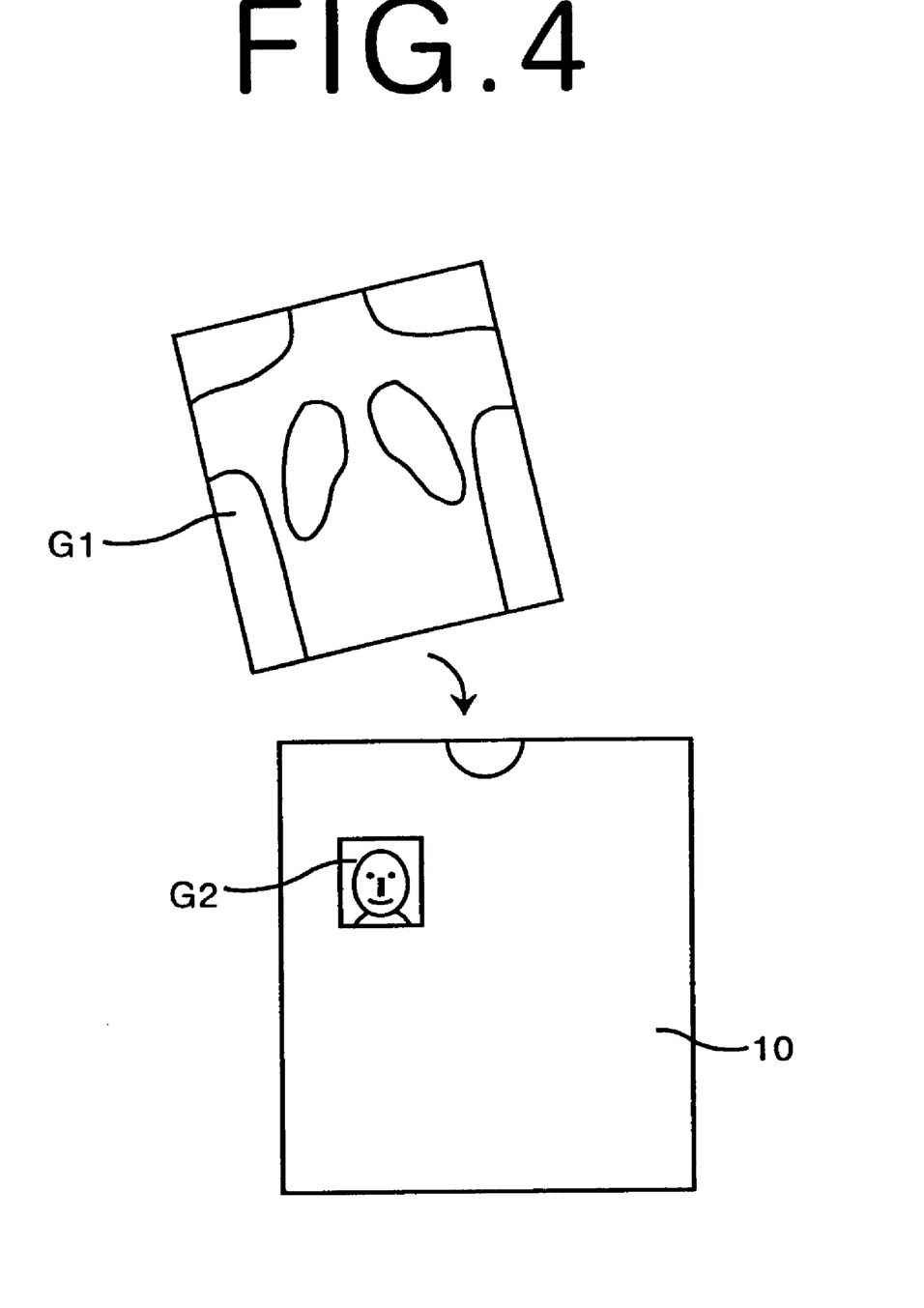
FIG. 4 is an explanatory view showing a different output form in the embodiment of FIG. 1

Also, in the embodiment described above, the medical image G1 and the face image G2 are reproduced and displayed on the monitor 4. Alternatively, the medical image G1 and the face image G2 may be outputted as hard copies with the printer 6. In cases where the medical image G1 and the face image G2 are printed as hard copies, when the outputted prints are seen, it can be recognized at a glance whether the medical image G1 is or is not the image of the patient to be subjected to a diagnosis. Therefore, the problems can be prevented from occurring in that a serious medical trouble, such as a mistake in a surgical operation, occurs due to a mix-up about who is to be subjected to a diagnosis. In such cases, as in the cases of the image reproduction on the monitor 4, the medical image G1 and the face image G2 may be combined with each other and printed on a single sheet of photosensitive material. Alternatively, the medical image G1 and the face image G2 may be printed on two different sheets of photosensitive material. By way of example, as illustrated in FIG. 4, in cases where the medical image G1 and the face image G2 are printed on two different sheets of photosensitive material, the face image G2 printed on a sheet of photosensitive material different from that for the medical image G1 may be attached to a bag 10, which accommodates the medical image G1. In such cases, when the bag 10 is seen, it can be confirmed at a glance which bag 10 accommodates the medical image G1 of which patient. Alternatively, the face image G2 may be attached directly to the medical image G1.

Further, in the embodiment described above, the face image signal S2 representing the face image of the patient is stored in the data base unit 1 together with the corresponding medical image signal S1. Alternatively, an associated face image signal S3, which represents an image of the face of a person associated with the patient, such as an image of the face of a member of the patient's family attending on the patient, an image of the face of the nurse in charge, an image of the face of the medical doctor in charge, or the like, may be stored in the data base unit 1 together with the corresponding medical image signal S1. As another alternative, an image signal representing an image of a fingerprint of the patient (a fingerprint image signal) may be stored in the data base unit 1 together with the corresponding medical image signal S1. In such cases, the fingerprint image signal is read from the data base unit 1 together with the corresponding medical image signal S1, and the fingerprint of the patient and the fingerprint image represented by the fingerprint image signal may be collated with each other. In this manner, the patient to be subjected to a diagnosis may be identified.

Figure 5:
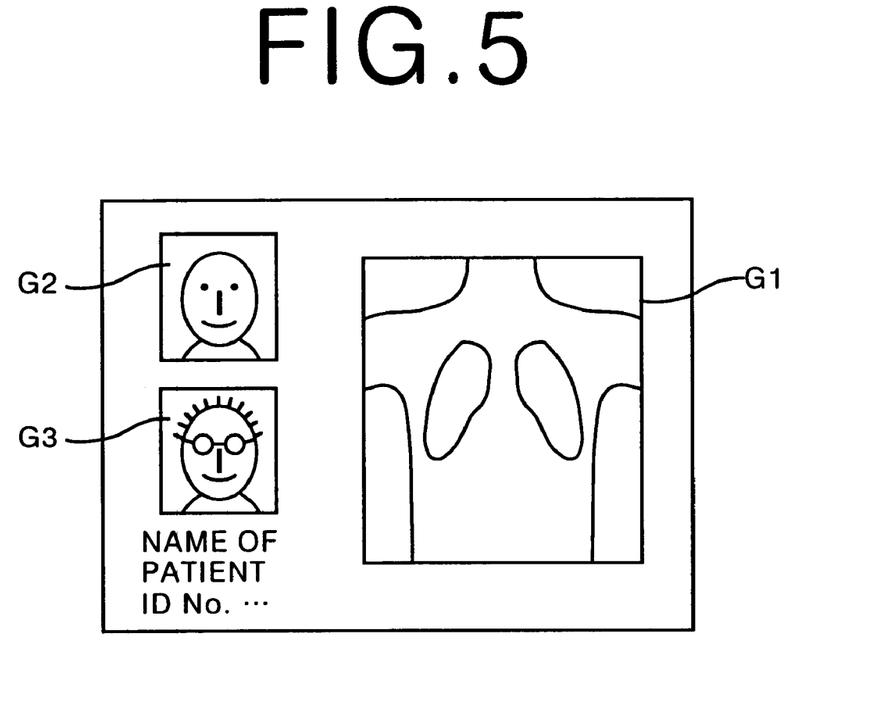
FIG. 5 is an explanatory view showing a medical image of a patient, a face image of the patient, and an associated face image of a person associated with the patient, which images are reproduced on a monitor.

Furthermore, in the embodiment described above, both the face image signal S2 representing the face image of the patient and the associated face image signal S3 may be stored in the data base unit 1. In cases where the face image signal S2 representing the face image of the patient and the associated face image signal S3 are stored in the data base unit 1, the face image signal S2 representing the face image of the patient and the associated face image signal S3 are stored together with the ID number of the patient in the data base unit 1, such that the correspondence relationship among them may be clear. In such cases, when the ID number of the patient is inputted from the terminal device 3, the medical image signal S1, which corresponds to the ID number of the patient, the face image signal S2, which corresponds to the medical image signal S1, and the associated face image signal S3, which corresponds to the medical image signal S1, are read from the data base unit 1 and fed into the terminal device 3. As illustrated in FIG. 5, on the monitor 4 connected to the terminal device 3, the medical image G1, which is represented by the medical image signal S1, the face image G2, which is represented by the face image signal S2, and an associated face image G3 of a person associated with the patient, which face image is represented by the associated face image signal S3, are reproduced. The medical image G1, the face image G2, and the face image G3 are displayed together with the name of the patient and the ID number of the patient on the monitor 4.

In the manner described above, the face image G2 and the associated face image G3 are reproduced together with the medical image G1. In such cases, an increased number of pieces of information, with which the patient is capable of being confirmed, can be obtained. Therefore, the confirmation as to whether the reproduced medical image G1 is or is not the one corresponding to the patient to be subjected to a diagnosis can be made more accurately.

In this case, the face image signal S2 representing the face image of the patient and the associated face image signal S3 are stored in the single data base unit 1. Alternatively, the face image signals S2, S2, . . . representing the face images of the patients and the associated face image signals S3, S3, . . . may be stored in different data base units, such that it may be clear which face image signal S2 corresponds to which associated face image signal S3.

Figure 6:
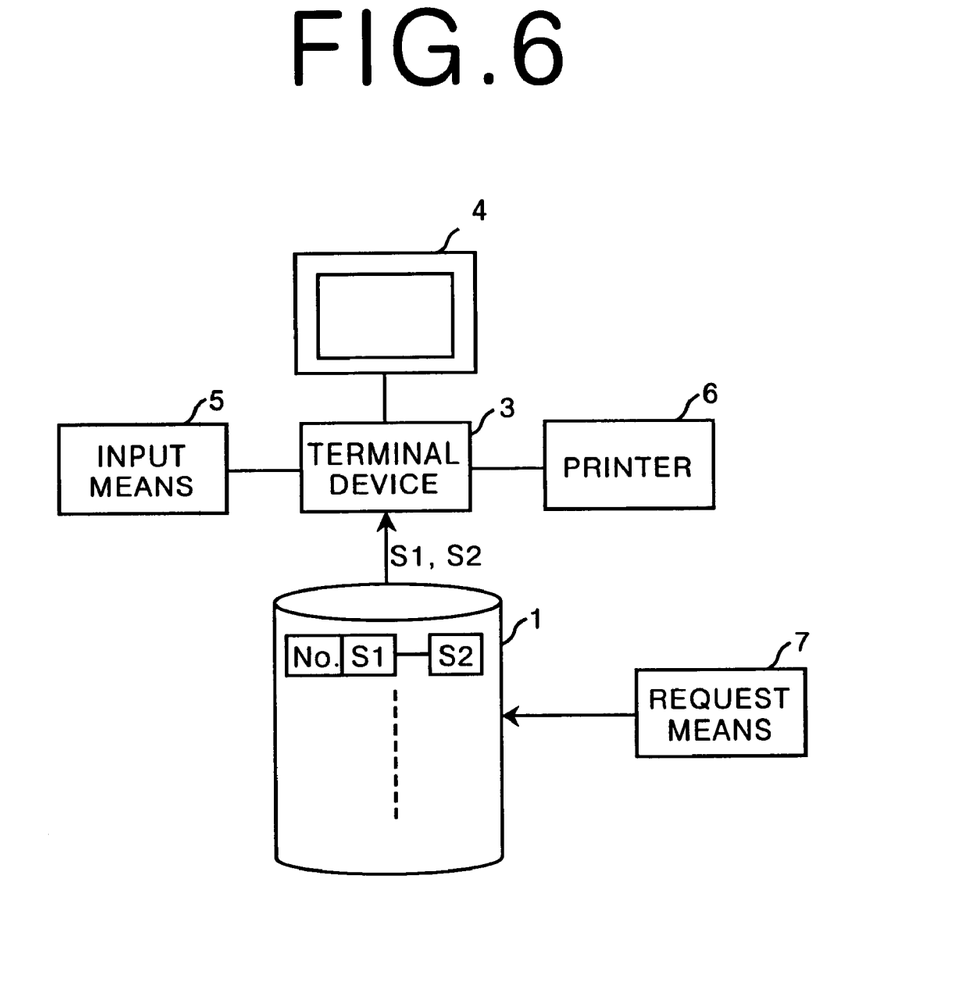
FIG. 6 is a schematic block diagram showing a different embodiment of the medical image output system in accordance with the present invention.

In cases where a comparatively long period (e.g., a period of approximately five years) has elapsed after a medical image signal S1 corresponding to a certain patient was stored in the data base unit 1, it may occur that the appearance of the patient changes, or the nurse in charge or the medical doctor in charge is altered. In such cases, if the medical image signal S1 corresponding to the patient is outputted together with the face image signal S2 representing the face image of the patient or the associated face image signal S3 (hereinbelow referred to as the face image signal S2, or the like), it will be difficult to make the confirmation as to whether the reproduced medical image G1 is or is not the one corresponding to the patient to be subjected to a diagnosis. Therefore, as in a different embodiment of the medical image output system in accordance with the present invention, which is illustrated in FIG. 6, request means 7 should preferably be provided. The request means 7 operates such that, in cases where a certain face image signal S2, or the like, has not been updated for a predetermined period after the certain face image signal S2, or the like, was stored in the data base unit 1, the request means 7 makes a request for storing a new face image signal S2, or the like, in the data base unit 1.

The request means 7 makes a judgment as to the date, on which the face image signal S2, or the like, was stored in the data base unit 1. In cases where the period occurring between the date, on which the face image signal S2, or the like, was stored in the data base unit 1, and the date, on which the judgment is made, is longer than a predetermined period, e.g. five years, the request means 7 makes a request for storing the new face image signal S2, or the like, in the data base unit 1. Specifically, for such purposes, an instruction for requesting the storing of the new face image signal S2, or the like, may be displayed on the monitor 4. Alternatively, an instruction for requesting the storing of the new face image signal S2, or the like, may be given with a voice. As another alternative, the monitor 4 may be caused to blink in order to make a request for the storing of the new face image signal S2, or the like. In cases where a request for the storing of the new face image signal S2, or the like, is made, for example, the ID number corresponding to the face image signal S2, or the like, should preferably be displayed on the monitor 4.

In cases where the request is made by the request means 7, the new face image signal S2, or the like, can be stored in the data base unit 1. Therefore, even if the appearance of the patient changes, or the nurse in charge or the medical doctor in charge is altered, the confirmation can be made accurately as to whether the outputted medical image signal is or is not the one corresponding to the patient to be subjected to a diagnosis.

In the embodiments described above, the medical image signal S1 and the face image signal S2 are retrieved by the utilization of the ID number of the patient. Alternatively, the signal retrieval may be performed by the utilization of the name of the patient.

In addition, all of the contents of Japanese Patent Application Nos. 11(1999)-122375 and 2000-129695 are incorporated into this specification by reference.

What is claimed is:

1. A medical image output system, comprising:
   i) first storage means for storing medical image signals, each of which represents a medical image of a patient,
   ii) second storage means for storing photographic image signals, each of which represents a photographic image of a somatic feature of a patient, and/or photographic image signals, each of which represents a photographic image of a person associated with a patient, such that it is clear which photographic image signal corresponds to which medical image signal stored in the first storage means, and
   iii) output means for operating such that, in cases where the output means outputs a medical image signal representing a medical image of a certain patient from the first storage means, the output means also outputs the photographic image signal, which corresponds to the outputted medical image signal, from the second storage means.

2. A system as defined in claim 1 wherein, in cases where both the photographic image signals, each of which represents a photographic image of a somatic feature of a patient, and the photographic image signals, each of which represents a photographic image of a person associated with a patient, are stored in the second storage means, the output means operates such that, when the output means outputs the medical image signal representing the medical image of the certain patient from the first storage means, the output means also outputs both the photographic image signal, which represents the photographic image of the somatic feature of the certain patient, and the photographic image signal, which represents the photographic image of the person associated with the certain patient, from the second storage means.

3. The system of claim 2, wherein the somatic feature comprises one of a face and a fingerprint of the patient, and wherein the person associated with the patient is a person other than the patient, such that the first and second storage means store image information for two different individuals.

4. A system as defined in claim 1 or 2 further comprising reproduction means for receiving the medical image signal and the corresponding photographic image signal from the output means, reproducing the medical image as a visible image from the received medical image signal, and reproducing the photographic image as a visible image from the corresponding photographic image signal.

5. A system as defined in claim 4, further comprising request means for operating such that, in cases where a certain photographic image signal has not been updated for a predetermined period after the certain photographic image signal was stored in the second storage means, the request means makes a request for storing a new photographic image signal in the second storage means.

6. The system of claim 5, wherein the somatic feature comprises one of a face and a fingerprint of the patient, and wherein the person associated with the patient is a person other than the patient, such that the first and second storage means store image information for two different individuals.

7. A system as defined in claim 1 or 2 further comprising request means for operating such that, in cases where a certain photographic image signal has not been updated for a predetermined period after the certain photographic image signal was stored in the second storage means, the request means makes a request for storing a new photographic image signal in the second storage means.

8. The system of claim 1, wherein the somatic feature comprises one of a face and a fingerprint of the patient, and wherein the person associated with the patient is a person other than the patient, such that the first and second storage means store image information for two different individuals.

* * * * *